(12) United States Patent
Milch

(10) Patent No.: US 9,295,532 B2
(45) Date of Patent: Mar. 29, 2016

(54) 3D INTRAORAL MEASUREMENTS USING OPTICAL MULTILINE METHOD

(75) Inventor: James R. Milch, Penfield, NY (US)

(73) Assignee: Carestream Health, Inc., Rochester, NY (US)

( * ) Notice: Subject to any disclaimer, the term of this patent is extended or adjusted under 35 U.S.C. 154(b) by 908 days.

(21) Appl. No.: 13/293,308

(22) Filed: Nov. 10, 2011

(65) Prior Publication Data
US 2013/0120532 A1 May 16, 2013

(51) Int. Cl.
| | |
|---|---|
| H04N 13/02 | (2006.01) |
| A61C 9/00 | (2006.01) |
| G01B 11/25 | (2006.01) |
| G06T 7/00 | (2006.01) |

(52) U.S. Cl.
CPC ............ *A61C 9/006* (2013.01); *G01B 11/2513* (2013.01); *G06T 7/0057* (2013.01); *G06T 2207/30036* (2013.01)

(58) Field of Classification Search
CPC .................. A61C 9/006; G06T 7/0057; G06T 2207/30036; H04N 13/02; G01B 11/2513
USPC ............................................. 348/45, E13.074
See application file for complete search history.

(56) References Cited

U.S. PATENT DOCUMENTS

| | | | | |
|---|---|---|---|---|
| 5,372,502 | A * | 12/1994 | Massen et al. | 433/215 |
| 5,650,621 | A * | 7/1997 | Tsuneta et al. | 250/311 |
| 6,510,244 | B2 | 1/2003 | Proesmans et al. | |
| 6,754,370 | B1 | 6/2004 | Hall-Holt et al. | |
| 7,126,699 | B1 * | 10/2006 | Wihl et al. | 356/625 |
| 7,146,036 | B2 | 12/2006 | An Chang et al. | |
| 2005/0046873 | A1 * | 3/2005 | Suzuki | 356/605 |
| 2005/0099638 | A1 * | 5/2005 | Quadling et al. | 356/603 |
| 2005/0254726 | A1 | 11/2005 | Fuchs et al. | |
| 2007/0057946 | A1 | 3/2007 | Albeck et al. | |
| 2007/0091319 | A1 * | 4/2007 | Sonda et al. | 356/600 |

(Continued)

FOREIGN PATENT DOCUMENTS

| | | |
|---|---|---|
| EP | 2 051 042 B1 | 11/2010 |
| JP | 2009-098146 A | 5/2009 |
| WO | 2011/013373 A1 | 2/2011 |

OTHER PUBLICATIONS

Guhring, Jens "Dense 3-D surface acquisition by structured light using off-the-shelf components", Videometrics and Optical Methods for 3D Shape Measurement, Proceedings of SPIE, vol. 4309 (2001) pp. 220-231.
International Search Report mailed Feb. 1, 2013 for International Application No. PCT/US2012/052178, 2 pages.

(Continued)

*Primary Examiner* — Christopher S Kelley
*Assistant Examiner* — Deirdre Beasley

(57) ABSTRACT

A method for mapping a sensor pixel array to an illumination pixel array according to a surface forms a group map by assigning each pixel on the sensor array to a corresponding group of an ordered set of groups, each group defined by a set of p adjacent pixels on the illumination pixel array by projecting and recording at least n projected images from a first set of n binary patterns, with transitions between pixels in each of the n binary patterns only at group boundaries. At least m images from a second set of m binary patterns are projected and recorded, with one or more transitions between pixels in each of the m binary pattern offset from group boundaries. At least p multiline images are projected and recorded. Lines in the recorded multiline images are correlated with lines in the multiline images according to the group map.

19 Claims, 17 Drawing Sheets

(56) References Cited

U.S. PATENT DOCUMENTS

| | | | |
|---|---|---|---|
| 2009/0103103 A1* | 4/2009 | Berner | 356/497 |
| 2009/0238449 A1* | 9/2009 | Zhang et al. | 382/165 |
| 2009/0322859 A1 | 12/2009 | Shelton et al. | |
| 2010/0034429 A1 | 2/2010 | Drouin et al. | |
| 2010/0085636 A1 | 4/2010 | Berner | |
| 2010/0253773 A1 | 10/2010 | Oota et al. | |
| 2010/0268069 A1* | 10/2010 | Liang | 600/425 |
| 2010/0311005 A1* | 12/2010 | Liang | 433/29 |
| 2011/0050859 A1 | 3/2011 | Kimmel et al. | |

OTHER PUBLICATIONS

Supplemental European Search Report, Application No. EP12847432, Jun. 19, 2015, 2 pages.

S. Logozzo, G. Franceschini, A. Kilpelä, M. Caponi, L. Governi, L. Blois: A Comparative Analysis of Intraoral 3d Digital Scanners for Restorative Dentistry. *The Internet Journal of Medical Technology*. 2011, vol. 5, No. 1, DOI: 10.5580/1b90, 19 pages, http://www.ispub.com:80/journal/the-internet-journal-of-medical-technology/volume-5- number-1/a-comparative-analysis-of-intraoral-3d-digital-scanners-for-restorative-dentistry.html.

* cited by examiner

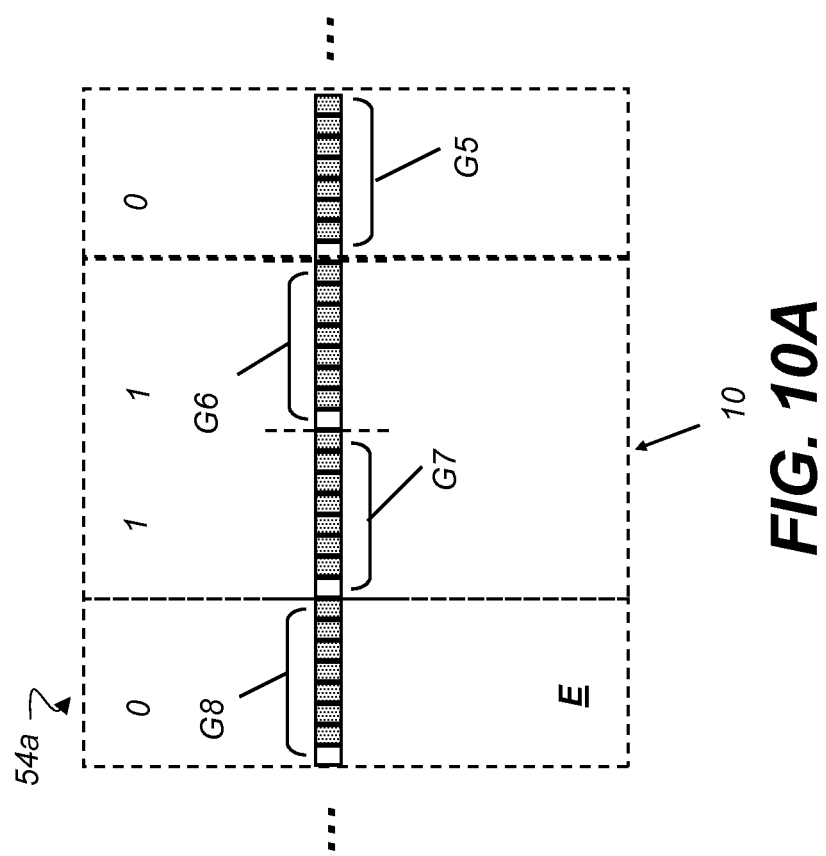

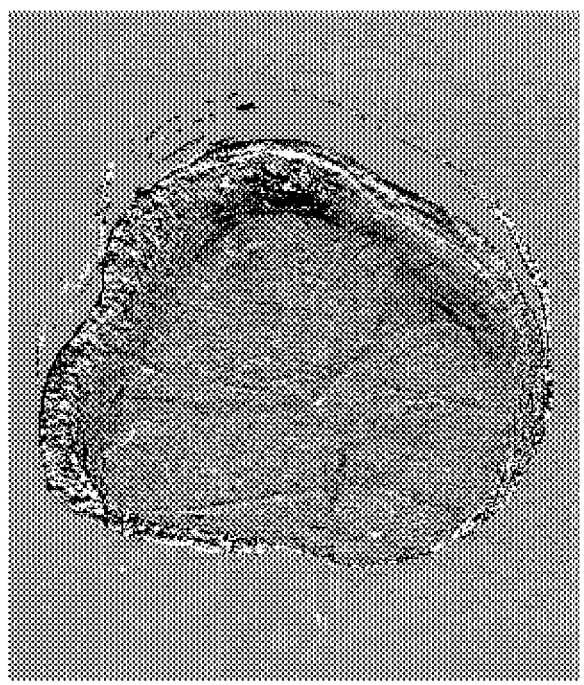

3D INTRAORAL MEASUREMENTS USING OPTICAL MULTILINE METHOD

FIELD OF THE INVENTION

The disclosure relates generally to the field of surface shape imaging and more particularly relates to intraoral surface imaging and measurement.

BACKGROUND OF THE INVENTION

Techniques have been developed for obtaining surface contour information from various types of objects in medical, industrial, and other applications. Optical 3-dimensional (3-D) measurement methods provide shape and depth information using images obtained from patterns of light directed onto a surface. Various types of imaging methods generate a series of light patterns and use focus or triangulation to detect changes in surface shape over the illuminated area.

Fringe projection imaging uses patterned or structured light and triangulation to obtain surface contour information for structures of various types. In fringe projection imaging, a pattern of lines of an interference fringe or grating is projected toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used effectively for surface contour imaging of solid, highly opaque objects and has been used for imaging the surface contours for some portions of the human body and for obtaining detailed data about skin structure. However, a number of technical obstacles have prevented effective use of fringe projection imaging of the tooth. One particular challenge with dental surface imaging relates to tooth translucency. Translucent or semi-translucent materials in general are known to be particularly troublesome for fringe projection imaging. Subsurface scattering in translucent structures can reduce the overall signal-to-noise (S/N) ratio and shift the light intensity, causing inaccurate height data. Another problem relates to high levels of reflection for various tooth surfaces. Highly reflective materials, particularly hollowed reflective structures, can effectively reduce the dynamic range of this type of imaging.

From an optical perspective, the structure of the tooth itself presents a number of additional challenges for fringe projection imaging. Teeth can be wet or dry at different times and along different surfaces and portions of surfaces. Tooth shape is often irregular, with sharp edges. As noted earlier, teeth interact with light in a complex manner. Light penetrating beneath the surface of the tooth tends to undergo significant scattering within the translucent tooth material. Moreover, reflection from opaque features beneath the tooth surface can also occur, adding noise that degrades the sensed signal and thus further complicates the task of tooth surface analysis.

One corrective measure that has been attempted to make fringe projection workable for contour imaging of the tooth is application of a coating that changes the reflective characteristics of the tooth surface itself. To compensate for problems caused by the relative translucence of the tooth, conventional tooth contour imaging systems apply a paint or reflective powder to the tooth surface prior to surface contour imaging. For the purposes of fringe projection imaging, this added step enhances the opacity of the tooth and eliminates or reduces the scattered light effects noted earlier. However, there are drawbacks to this type of approach. The step of applying a coating powder or liquid adds cost and time to the tooth contour imaging process. Because the thickness of the coating layer is often non-uniform over the entire tooth surface, measurement errors readily result. More importantly, the applied coating, while it facilitates contour imaging, can tend to mask other problems with the tooth and can thus reduce the overall amount of useful information that can be obtained.

Even where a coating or other type of surface conditioning of the tooth is used, however, results can be disappointing due to the pronounced contours of the tooth surface. It can be difficult to provide sufficient amounts of light onto, and sense light reflected back from, all of the tooth surfaces. The different surfaces of the tooth can be oriented at 90 degrees relative to each other, making it difficult to direct enough light for accurately imaging all parts of the tooth.

It can be appreciated that an apparatus and method that provides accurate surface contour imaging of the tooth, without the need for applying an added coating or other conditioning of the tooth surface for this purpose, would help to speed reconstructive dentistry and could help to lower the inherent costs and inconvenience of conventional methods, such as those for obtaining a cast or other surface profile for a crown, implant, or other restorative structure.

SUMMARY OF THE INVENTION

An object of the present invention is to advance the art of surface contour detection of teeth and related intraoral structures. Embodiments of the present invention provide 3-D surface information about a tooth by illuminating the tooth surface with an arrangement of light patterns that help to more closely map pixel locations on a digital imaging array with pixel locations from an illumination device. Advantageously, the present invention can be used with known illumination and imaging component arrangements and is adapted to help reduce ambiguity of sensed patterns when compared against conventional contour detection methods.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for mapping a sensor pixel array to an illumination pixel array according to a surface, the method executed at least in part on a computer and comprising: forming a group map by assigning each pixel in a plurality of pixels on the sensor array to a corresponding group of an ordered set of groups, wherein each group is defined by a set of p adjacent pixels on the illumination pixel array and wherein each group is defined by a group boundary by: projecting and recording at least n images from a first set of n binary patterns onto the surface, wherein a bright to dark or dark to bright transition between pixels in each of the n binary patterns occurs only at one or more of the group boundaries; projecting and recording at least m images from a second set of m binary patterns onto the surface, wherein one or more bright to dark or dark to bright transitions between pixels in each of the m binary patterns are offset from one or more of the group boundaries; projecting and recording at least p multiline images onto the surface, wherein each multiline image projects a line within each group; correlating lines in the recorded multiline images with lines in the projected multiline images according to the group map; and storing the correlation in a computer-accessible memory, wherein n and m are integers greater than or equal to 1 and p is an integer greater than or equal to 2.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 10A shows a portion of the illumination array for forming a multiline image.

FIG. 16 is a difference map combining the results of FIGS. 15A and 15B.

DETAILED DESCRIPTION OF THE INVENTION

Figure 1:
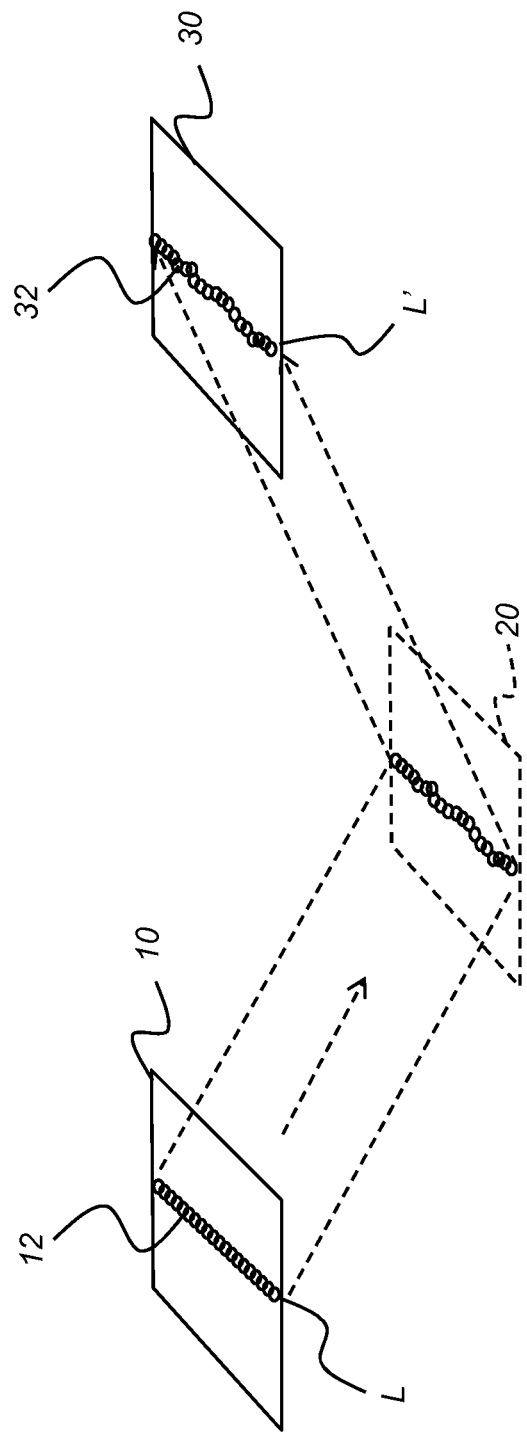
FIG. 1 is a schematic diagram that shows mapping a sensor pixel array to an illumination array according to a surface.

The following is a detailed description of the preferred embodiments of the invention, reference being made to the drawings in which the same reference numerals identify the same elements of structure in each of the several figures. Where they are used, the terms "first", "second", and so on, do not necessarily denote any ordinal, sequential, or priority relation, but are simply used to more clearly distinguish one element or set of elements from another.

The schematic diagram of FIG. 1 shows, with the example of a single line of light L, how patterned light is used for obtaining surface contour information. A mapping is obtained as an illumination array 10 directs a pattern of light onto a surface 20 and a corresponding image of a line L' is formed on an imaging sensor array 30. Each pixel 32 on imaging sensor array 32 maps to a corresponding pixel 12 on illumination array 10 according to modulation by surface 20. Shifts in pixel position, as represented in FIG. 1, yield useful information about the contour of surface 20. It can be appreciated that the basic pattern shown in FIG. 1 can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the light pattern as needed for the mapping sequence.

Figure 2B:
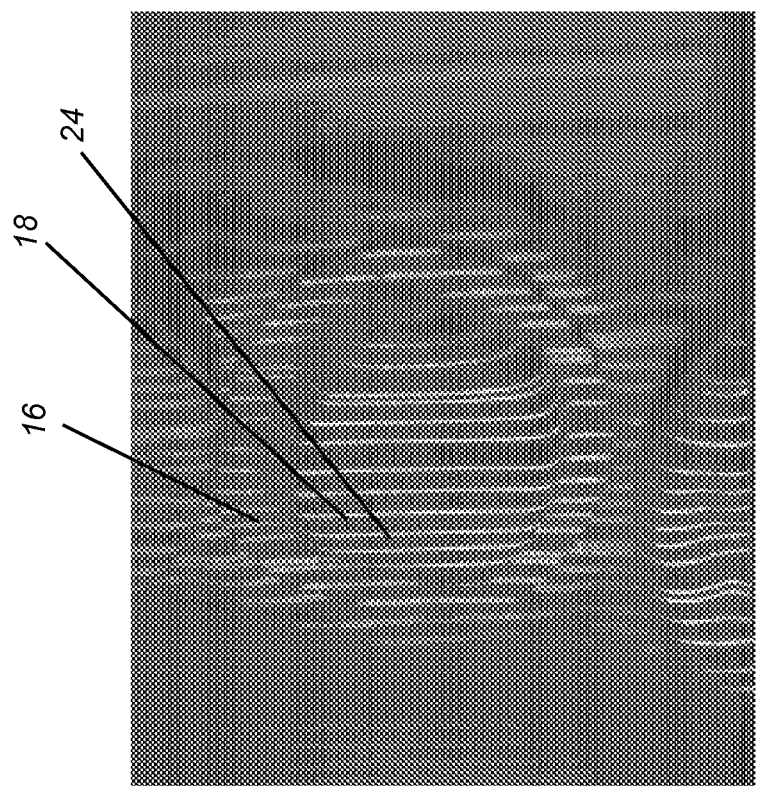
FIG. 2B shows illumination of a tooth surface with multiple lines of light.
Figure 2A:
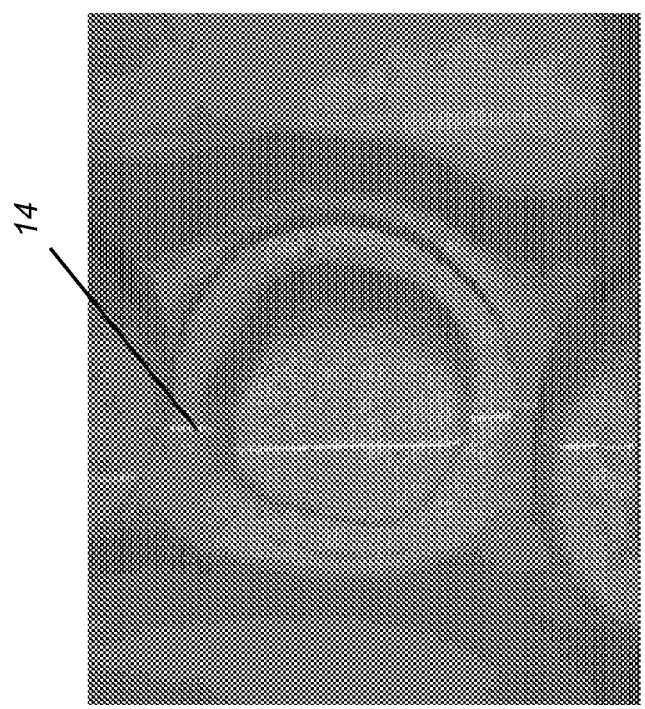
FIG. 2A shows illumination of a tooth surface with a single line of light.

FIGS. 2A and 2B show aspects of one problem with conventional approaches for using patterned light to obtain surface structure information from the human tooth. FIG. 2A shows illumination with a single line of light 14 onto the tooth, with pronounced shifting of the illumination at the tooth edges. Projection of a single line in this manner, scanned across the tooth and imaged at numerous points during the scan, can provide accurate information about portions of the surface area; however, some information is lost even with this method, such as where line segments are separated from each other. FIG. 2B shows surface imaging using a pattern with multiple lines of light. Where there are abrupt transitions along the surface, it can be difficult to positively identify the segments that correspond to each projected line and mismatches can easily occur, leading to inaccurate conclusions about surface characteristics. For example, it can be difficult to determine whether line segment 16 is from the same line of illumination as line segment 18 or adjacent line segment 24.

Embodiments of the present invention address the problem of surface contour mapping using a sequence of projected images that help to better correlate pixels on the imaging sensor array with projected lines from the illumination array. To do this, embodiments of the present invention use an arrangement of binary images to group pixels on the imaging sensor array with corresponding pixels on the illumination pixel array. A group map is formed by assigning pixels on the sensor array to an ordered set of groups, each group having a fixed number of pixels.

Figure 3:
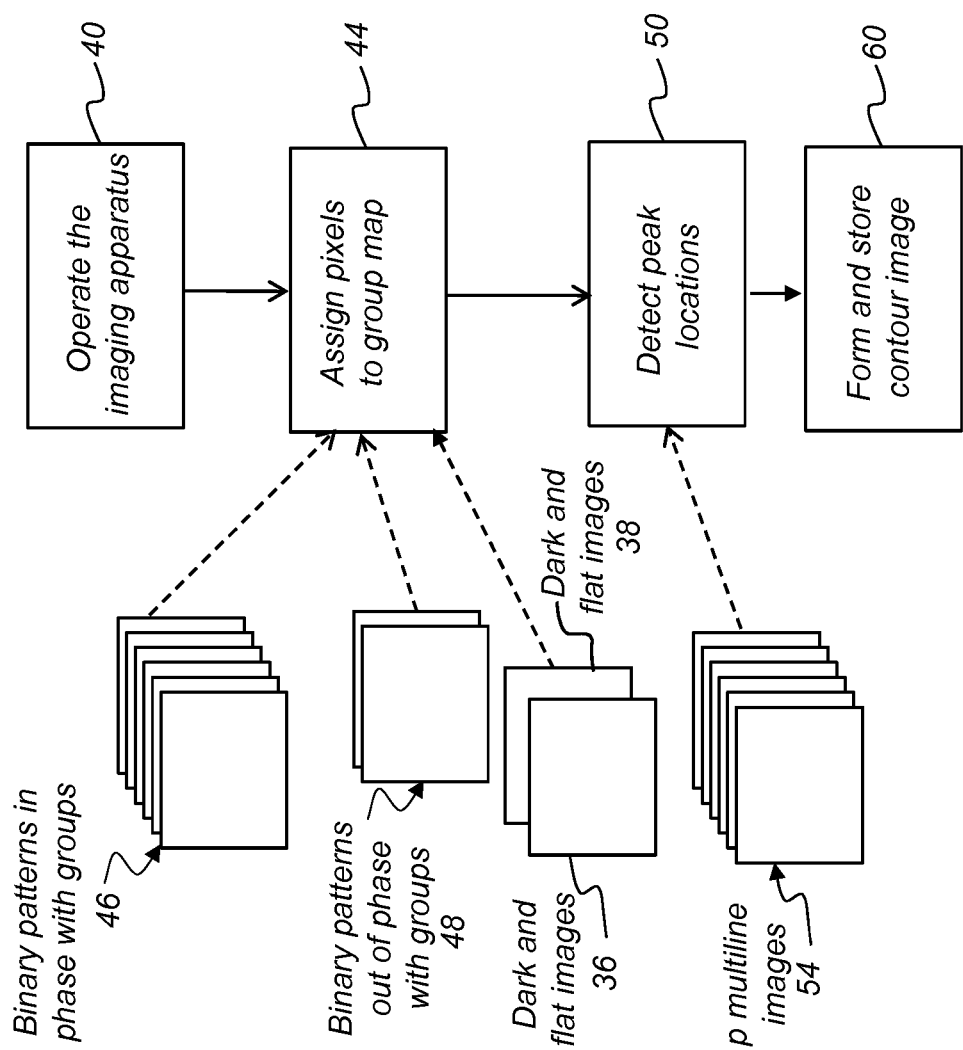
FIG. 3 is a logic flow diagram that shows a sequence for obtaining surface contour image data according to an embodiment of the present invention.

Referring to the flow diagram of FIG. 3, there is shown a sequence of image projection, detection, and processing steps used for surface contour detection and executed at least in part on a computer according to an embodiment of the present invention. In an image capture step 40, the operator positions the imaging apparatus and captures a series of images, as described subsequently. The images consist of a number n of binary patterns 46 and m binary patterns 48 and p multiline images 54 and can be captured in any order. Once the images are captured, a pixel assignment step 44 executes, in which pixels on the image sensor array are assigned to a group map that corresponds to pixels on the illumination array. Images for the group mapping are from binary patterns 46 and 48, described in more detail subsequently. An additional dark image 36, with no illumination, and flat image 38 with full frame illumination are also obtained to help in signal processing, as described subsequently.

Continuing with the sequence of FIG. 3, a set of p multiline images 54 is also obtained, from which peak locations, that is, locations of highest intensity, can be detected in a location detection step 50. A mapping step 60 then forms and stores the contour image in a memory, such as in a temporary display memory that is associated with a display monitor, for example.

Relative to FIG. 1, a binary pattern has one or more bright bands that are two or more pixels wide on illumination array 10. A multiline image has one or more bright bands that are one pixel wide on illumination array 10. The multiline image has at least one bright-to-dark or dark-to-bright transition within each group of pixels.

Figure 4:
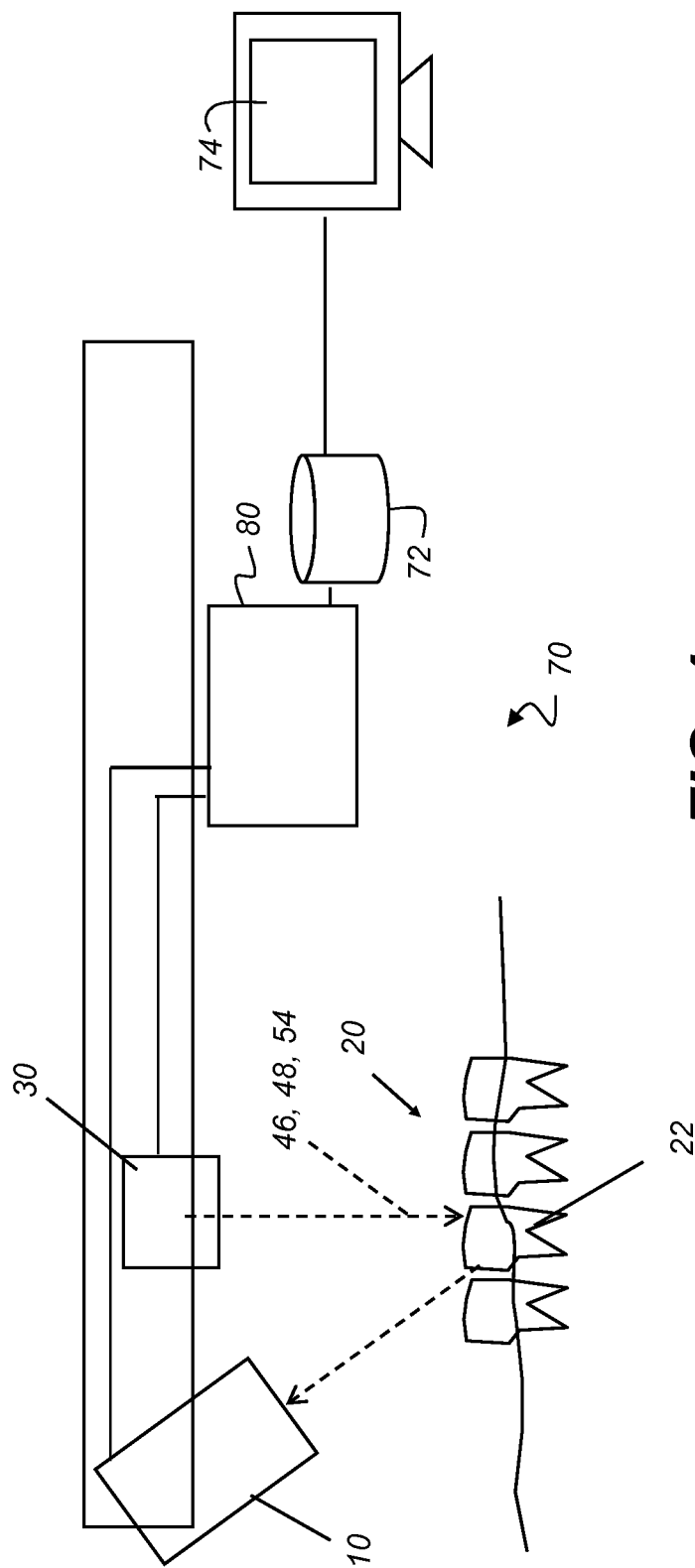
FIG. 4 is a schematic diagram showing an imaging apparatus.

The schematic diagram of FIG. 4 shows an imaging apparatus 70 for projecting and imaging the binary patterns 46 and 48 and multiline images 54. A control logic processor 80, or other type of computer controls the operation of illumination array 10 and imaging sensor array 30. Image data from surface 20, such as from a tooth 22, is obtained from imaging sensor array 30 and stored in a memory 72. Control logic processor 80 processes the received image data and stores the mapping in memory 72. The resulting image from memory 72 is then optionally displayed on a display 74. Memory 72 may also include a display buffer.

Figure 5:
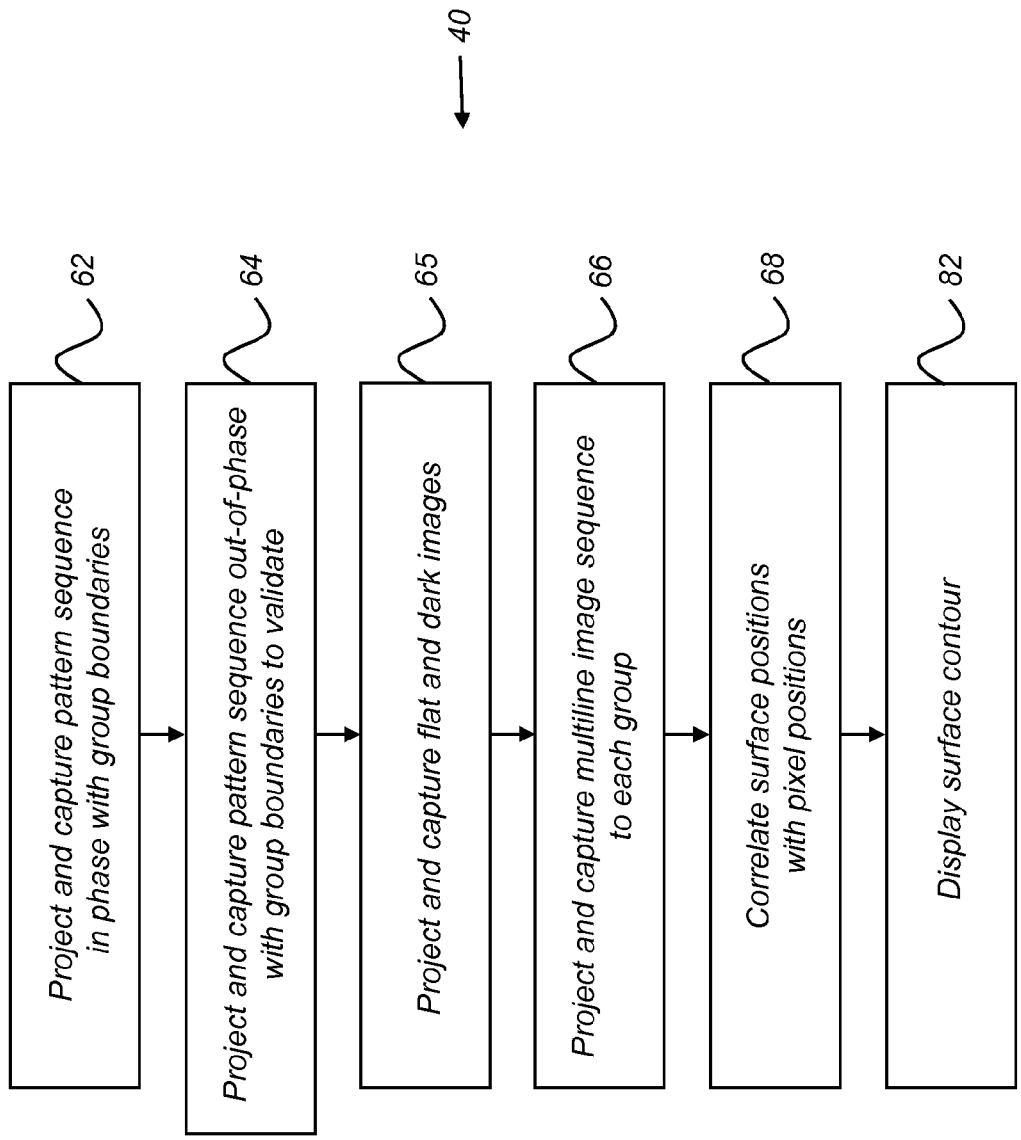
FIG. 5 is a logic flow diagram that shows an image projection and recording sequence.

The logic flow diagram of FIG. 5 shows the image projection and capture sequence described as image capture step 40 in FIG. 3 and using the imaging apparatus 70 of FIG. 4 in more detail. A first binary pattern recording step 62 records at least n images from a first set of n binary patterns projected onto the surface, in which transitions between pixels occur only at group boundaries, as described subsequently. This set of n images is described as being "in-phase" with the group arrangement. A second binary pattern recording step 64 then records m binary patterns projected onto the surface, in which one or more transitions between pixels in each of the m patterns are offset from group boundaries, again described in more detail subsequently. This set of m images is described as being "out-of-phase" with the group arrangement, with at least one transition within a group. A dark and flat image recording step 65 then records dark field and flat field images. The combination of images recorded from recording steps 62, 64, and 65 are then used for forming the group map in pixel assignment step 44 of FIG. 3. A multiline image recording step 66 projects onto the surface and records at least p multiline images, as described in more detail subsequently. Following image capture, a correlation step 68 then correlates surface positions with pixel positions on image sensor array 30 as part of mapping step 60 in FIG. 3. An optional display step 82 then displays the surface contour obtained from the mapping.

Forming the Group Map

Figure 6:
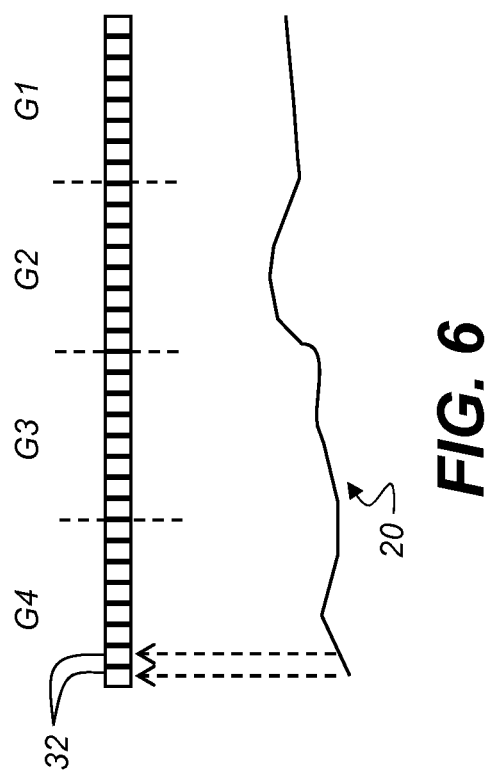
FIG. 6 is a schematic diagram that shows part of a row of pixels on the imaging sensor array.
Figure 7:
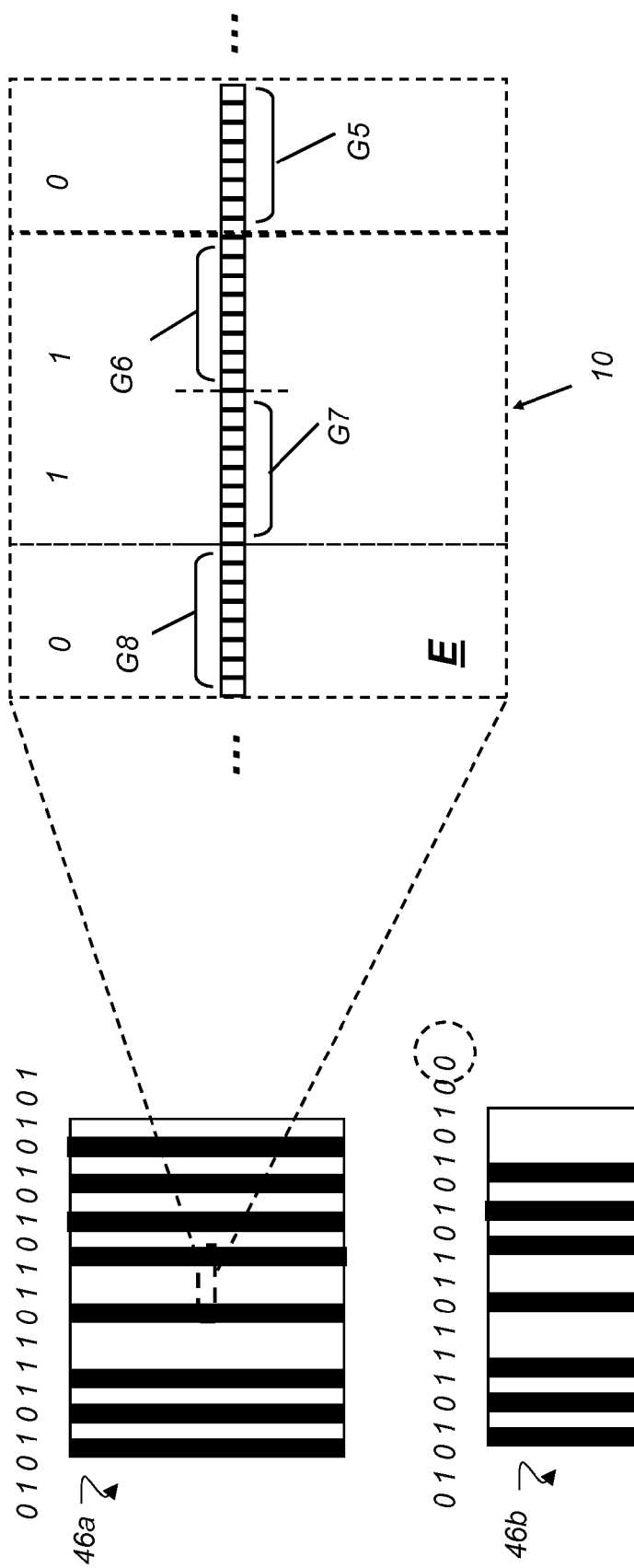
FIG. 7 is a schematic diagram that shows in-phase binary projected patterns for group mapping.
Figure 8:
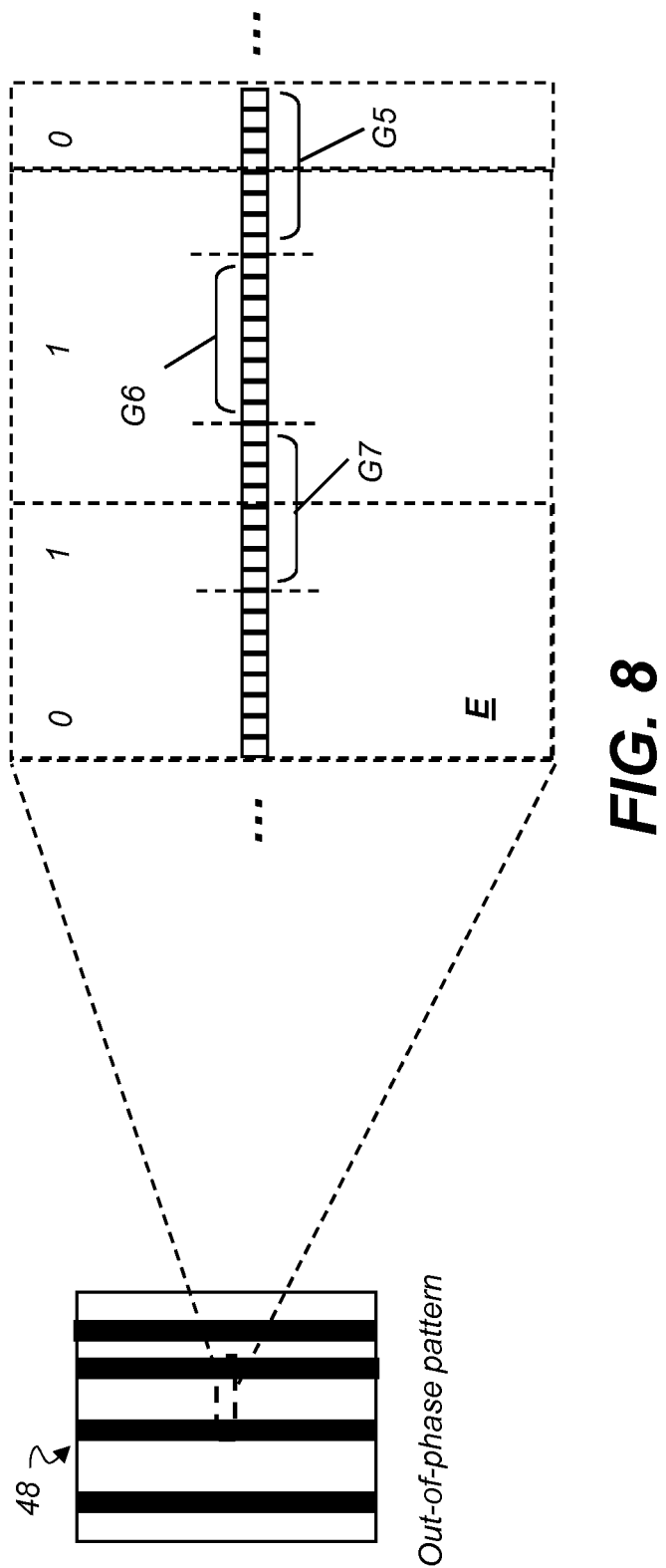
FIG. 8 is a schematic diagram that shows a binary projected pattern of a second out-of-phase set.

Schematic diagrams of FIGS. 6, 7, and 8 show various aspects of the process for forming the group map according to an embodiment of the present invention. FIG. 6 shows part of a row of pixels 32 on imaging sensor array 30 corresponding to positions on surface 20. Each group has a predetermined number p of adjacent pixels 32, with eight pixels 32 per group in the example mapping that is shown. Vertical dashed lines in FIGS. 6-8 indicate group boundaries. At a group boundary, wherein each group has p pixels numbered from 0, 1, 2, . . . (p−1), the (p−1)th pixel of one group is adjacent to the 0th pixel of the next, or adjacent, group in the row; the space between these two adjacent pixels, with one pixel in each of two adjacent groups, defines a group boundary. The group boundary is considered to be "shared" by two adjacent groups. Two sequences of projected binary patterns are used to establish the group map. The schematic diagram of FIG. 7 shows the first pattern. Here, n images from a set of n binary patterns are projected from illumination array 10 in which each row is arranged according to groups. Representative eight-pixel groups G8, G7, G6, and G5 are shown, numbered in descending order from right to left in this example. Two of the n binary patterns 46a and 46b are shown, with binary 1, 0 representation shown for respective dark (off or 0)/bright (on or 1) bands that have transitions from bright to dark or, alternately, from dark to bright, at group boundaries. In the example shown at enlarged portion E, a 0110 portion of the binary pattern 46a is represented, with transitions between 0 and 1 occurring only at group boundaries. Binary pattern 46b is the next binary pattern in sequence, changing only one bit from the binary pattern at 46a. Consistent with an embodiment of the present invention, the successive binary patterns are arranged in a sequence that emulates a Gray code, in which each successive pattern (x) changes by only one bit from the previous pattern (x−1). This use of a Gray code emulation is advantaged for helping to reduce ambiguity in determining which corresponding pixel on imaging sensor array 30 maps to a group defined on illumination array 10 (FIG. 1). Bright bands in the binary patterns 46a and 46b, corresponding with binary number 1 in FIGS. 7 and 8, have a width that is in integer increments of a group of pixels, so that a bright band will be as wide as one, two, or more than two groups of pixels from the illuminator array. In the example of FIG. 7, in which a group has 8 pixels, a bright band in the binary pattern 46a or 46b is 8, 16, 24, 32, or some other integer multiple of 8 pixels wide.

Figure 9:
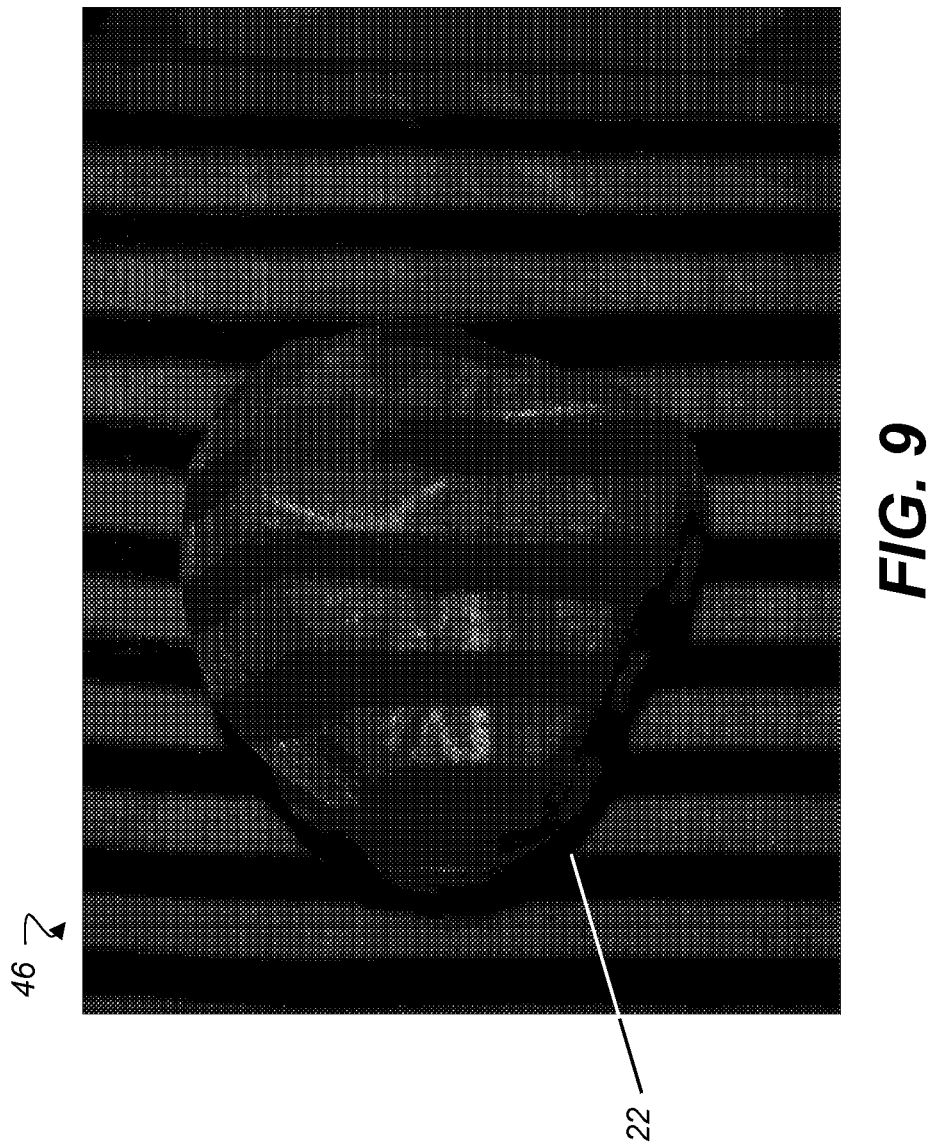
FIG. 9 shows a single projected binary pattern.

The schematic diagram of FIG. 8 shows projection of one of the second set of m binary patterns 48. Here, one or more of the binary 0/1 or 1/0 transitions between pixels are offset from group boundaries. In the example shown, group G7 spans across the corresponding transition that is offset from its boundary with group G6. Similarly, a transition is offset from the border of group G5, splitting pixels in this group into those on one side of the transition and those on the other. This use of an offset or out-of-phase pattern is a feature of embodiments of the present invention and acts as a further check on group boundaries, to help resolve possible ambiguity between group assignments. FIG. 9 shows a single projected binary pattern 46 relative to a typical tooth.

Consistent with an embodiment of the present invention, an analog filter is applied to each of the binary pattern images. This has been found to be of value in areas of low signal content. Alternately, thresholding using a digital filter can be employed for this purpose.

There is some level of signal (a "cut-off point") in the flat image 38 (FIG. 3) that can be too low for accurate comparisons. This level can simply be set as a parameter for the processing software. It can also be calculated adaptively by finding all the peaks in the multiline image, as described subsequently, and noting the "flat" values at those peak positions. Pixels with levels below this cutoff point are simply declared to be indeterminate, having unknown states, and are not processed further.

After thresholding, the n block images are combined at each pixel to form an n-bit number. This number is then translated through the inverse of an encoding table to identify the corresponding group number. In the absence of errors, this completes the block image processing.

Geometrically, when moving from one side of the image to the other along a row, the group number must change monotonically. (The numbers on different rows may not align, but within each row, they are monotonic.) This makes it possible to 'proofread' the group numbers on each row, discarding places where noise has disturbed the expected monotonic increase of group number.

Multiline Images

Figure 10B:
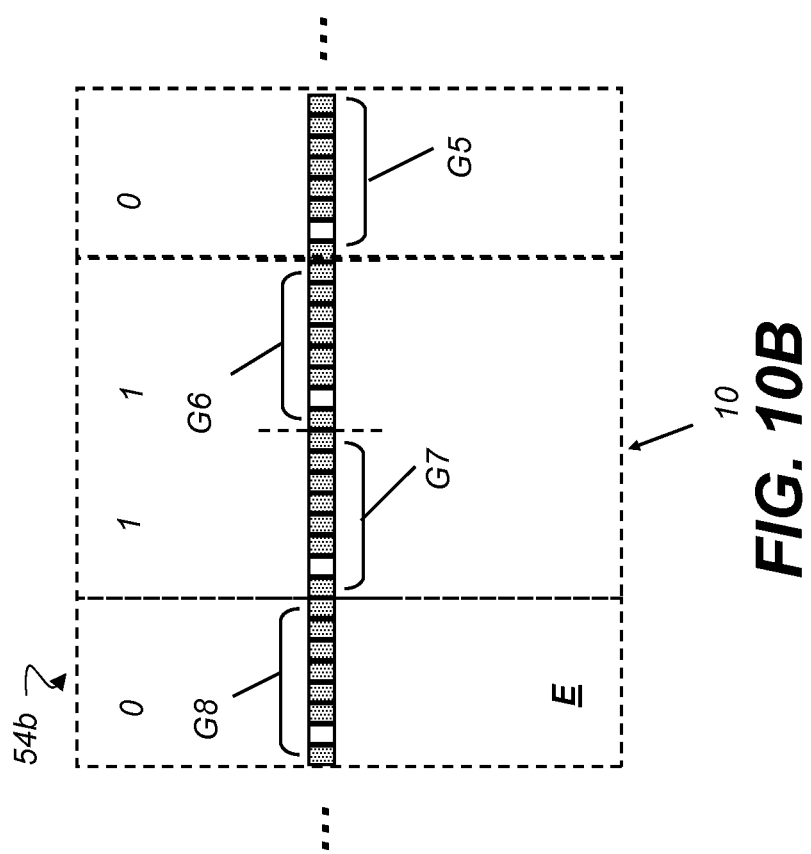
FIG. 10B shows another portion of the illumination array for forming a multiline image.
Figure 11:
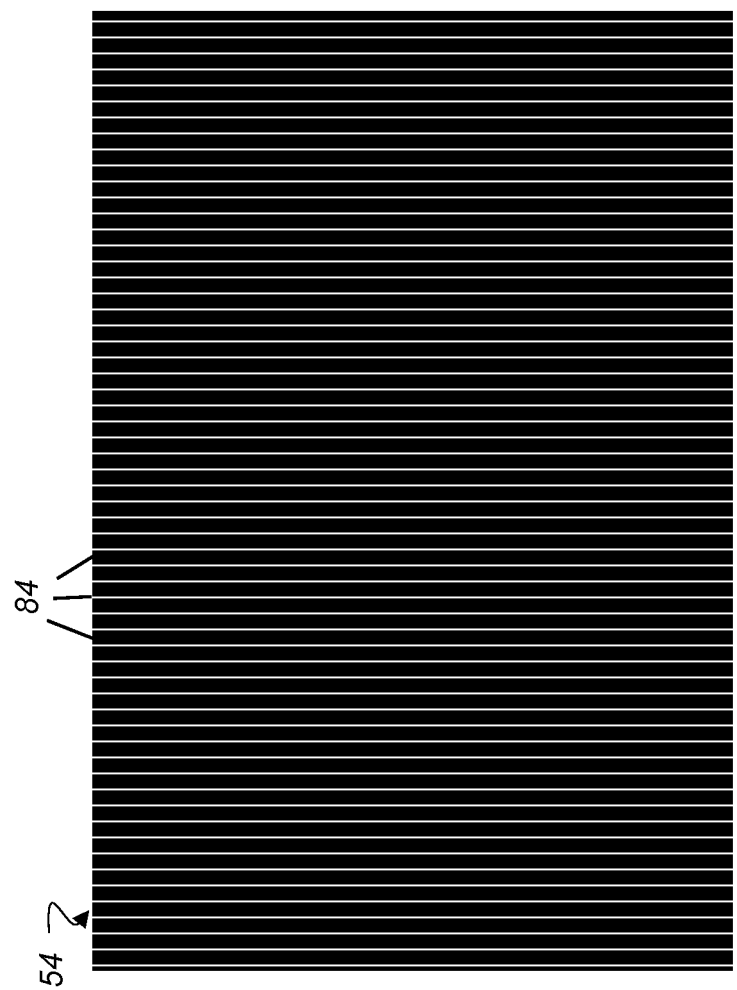
FIG. 11 is a plan view of an exemplary multiline image.
Figure 12:
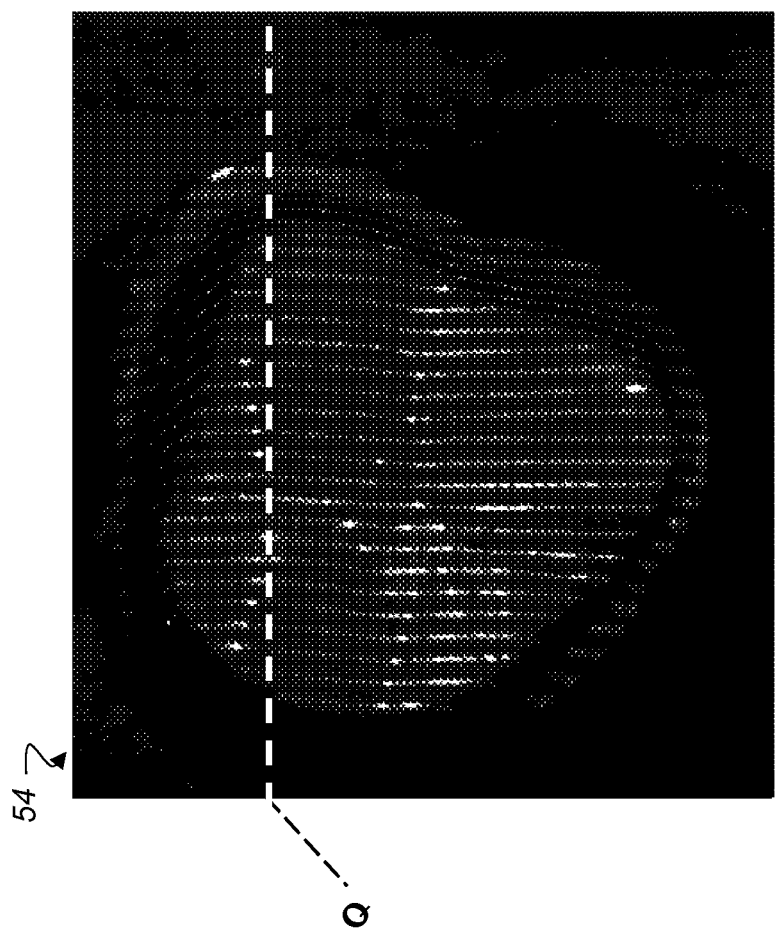
FIG. 12 is a plan view of a projected multiline image on a tooth.
Figure 13:
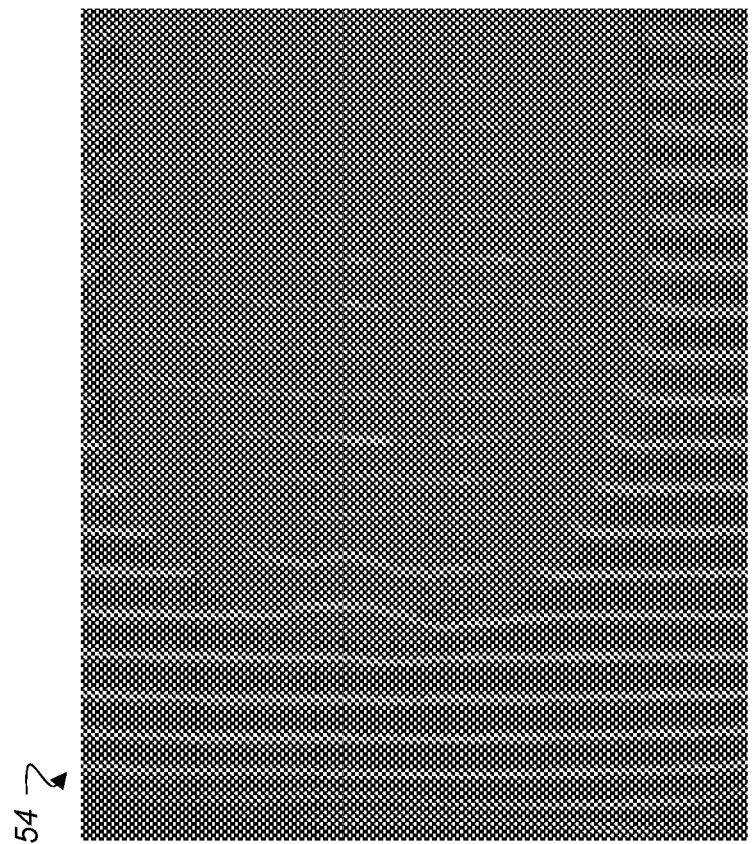
FIG. 13 is another plan view of a projected multiline image on a tooth.

As was noted with respect to the sequences shown in FIGS. 3 and 5, a set of at least p multiline images is projected onto the surface, in addition to the n in-phase and m out-of-phase images. The schematic diagram of FIG. 10A shows, for a single row of illumination array 10, a portion of a first multiline image 54a in which the left-most pixel in each group is illuminated to form a line. FIG. 10B shows another multiline image 54b in which the next pixel in each group is illuminated. Where each group has 8 pixels, as in the examples shown herein, this sequence repeats so that there are at least 8 multiline images, one for each pixel in each group. Transitions from dark to light or from light to dark are only with respect to a single pixel width in a multiline image; each bright band of light that forms a line is a single pixel wide. Each multiline image projects a single line within each group, so that there is at least one bright-to-dark or dark-to-bright transition between adjacent group boundaries in a multiline image. In general, where each group has a number p adjacent pixels, at least p multiline images are projected onto the surface and recorded. In addition, more than 8 multiline images can be projected and recorded, in cyclical or other sequencing arrangement. FIG. 11 shows a multiline image 54 with a line 84 within each group as projected from illumination array 10. FIGS. 12 and 13 show exemplary multiline images 54 as projected onto the surface 20 and recorded by imaging sensor array 30. The dashed line Q in FIG. 12 indicates one row of pixels on imaging sensor array 30.

Consistent with an embodiment of the present invention, each of the multiline images is analyzed as a set of independent rows, to locate each intensity peak in the row. This is done in two steps. Initially, a combination of smoothing filter and differentiating filter locates pixels where there is a peak signal. Then, a parabola is fit to the observed points around the identified pixel in order to locate the peak with sub-pixel accuracy. The background around the peak is also estimated to provide additional information on relative peak height. A candidate peak can be dropped from the list of peaks if it is too weak or too close to another peak. The result of the analysis is a long peak list (30,000 to 100,000 for a typical imaging sensor array) of precise locations where intensity peaks were observed.

Combining the Group Map and Peak List

In the absence of noise or errors, combination of group and peak data is driven by the list of peaks, which contains the peak location in x and y (i.e. pixel location along the row and the row number), the peak height, the peak width, and the image from which it came (multiline images 1 to p). For each peak, the group number from the nearest pixel in the Group Map is retrieved. The group number and image number are combined to calculate the line on the illuminator, 1 to 480 in a 480 line image. This gives three essential "pixel positions" for the peak: the x and y location on the imager and the x location on the illuminator, just as would be obtained from a single projected point.

Next, an approximate position of the point on the tooth or other surface is calculated, using the three pixel positions and calibration parameters. These approximate positions are processed, using information known from calibration, to determine an accurate location (x, y, z) on the surface. All of these locations form the point cloud, which is the final output of the combination algorithm.

The in-phase binary patterns 46 and out-of-phase binary patterns 48 are combined to improve the accuracy of the mapping and to compensate and identify various physical effects that might otherwise induce errors in the Group Map. For the explanation that follows:

(1) the term "phase" relates to the image number (1–p) from which a peak came;

(2) the numerical labeling of illuminator lines is assumed to increase from right to left on the imaging sensor array; a monotonic rule states that the group number must increase from right to left along a row; and (3) there are assumed to be multiple (at least 2 or 3) imaging sensor array pixels for every illuminator array pixel.

Figure 14:
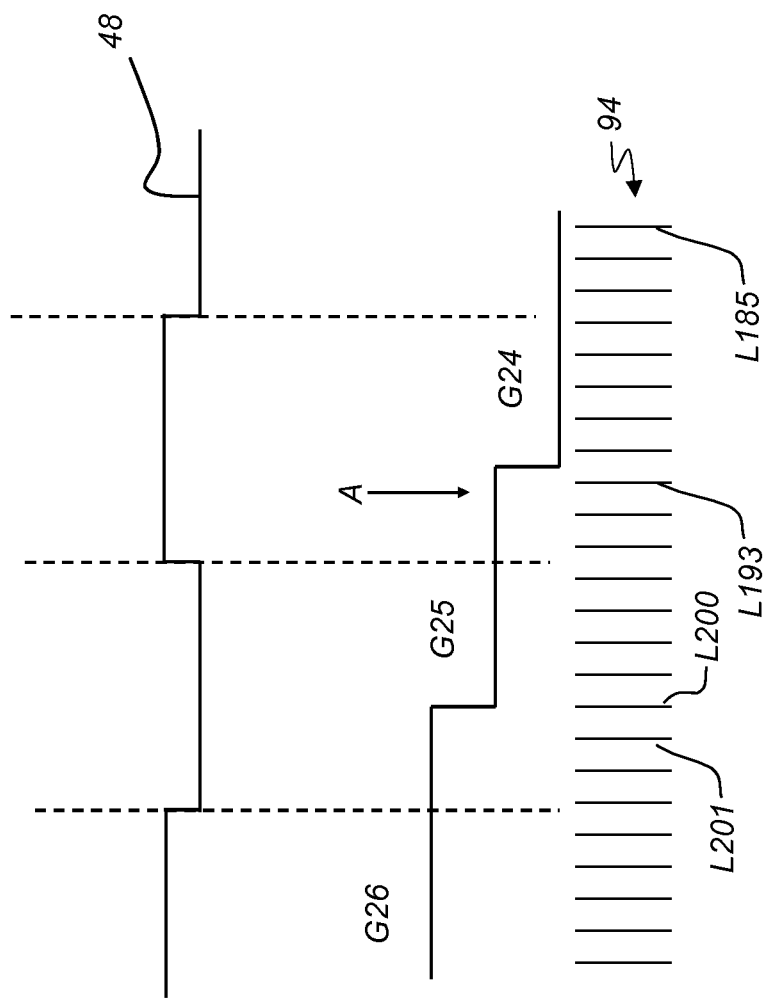
FIG. 14 is a schematic diagram showing how data from binary pattern images and multiline images are combined.

Referring to the schematic diagram of FIG. 14, a portion of an out-of-phase binary pattern 48 is shown, with corresponding lines from a first captured image frame from the multiline images represented. A number of representative lines L185, L193, L200, and L201 are shown. A portion of the group mapping is also shown for groups G24, G25, and G26. Corresponding illuminator array pixel center positions 94 are also shown.

Lines L193 to L200 are in group G25. The out-of-phase binary pattern 48 changes between groups, as described previously. An arrow A marks a peak observed in a phase 1 multiline image. (The phase numbers count from right to left in this example arrangement.) Errant group codes can be detected in a number of ways, including the following:

(i) The group code should change only near phases 1 and 8. For peaks in phases 2-7, all the pixels around a peak center should have the same group code.

(ii) Assume there is a peak in a phase 1 image and the group code is G25. That must be line L193 on the illuminator array, unless there is an error and is actually group G24, misread. If this is the case, it is line L185. Alternately, it could be line L201 in group 26. However, the out-of-phase signal of binary pattern 48 is unambiguously high around line L193 and low around lines L185 and L201. Checking the out-of-phase signal verifies the group code for phases 1 and 8, as well as phases 2 and 7.

(iii) Keeping track of the group code associated with each peak on a row; from right to left, the group codes should increase monotonically. A code may be skipped, but the group number should not decrease. If a decrease is observed, a potential problem is indicated.

Dark and Flat Images

Dark and flat images 36 and 38 are obtained as described in the sequence of FIG. 3. These images can be averaged to provide a measure of intensity that is used as a threshold to differentiate bright from dark intensities to help improve the signal mapping in pixel assignment step 44 (FIG. 3).

It is noted that the sequence of image projections and recording can be followed in any suitable order for the methods of the present invention. Moreover, multiline images and binary patterns can be interspersed, rather than obtained in any fixed order.

Figures 15A, 15B:
FIGS. 15A and 15B compare results for uncoated and coated teeth.

FIGS. 15A and 15B compare results of processing using the method of the present invention for an uncoated tooth 90 and for a coated tooth 92, that is, a tooth coated with a powder or other material, as is employed with tooth surface imaging systems that have been commercially available. As shown, results for uncoated tooth 90 compare favorably to those for coated tooth 92, without the need to prepare the tooth.

FIG. 16 shows a difference map 98 from combining the images for uncoated and coated teeth 90 and 92.

Consistent with at least one embodiment of the present invention, a computer executes a program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In the context of the present disclosure, the act of "recording" images means storing image data in some type of memory circuit in order to use this image data for subsequent processing. The recorded image data itself may be stored more permanently or discarded once it is no longer needed for further processing. An "ordered set" has its conventional meaning as used in set theory, relating to a set whose elements have a non-ambiguous ordering, such as the set of natural numbers that are ordered in an ascending sequence, for example.

It is noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types. Computer-accessible memory of various types is provided on different components throughout the system for storing, processing, transferring, and displaying data, and for other functions.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for mapping a sensor pixel array to an illumination pixel array according to a surface, comprising:
    forming a group map by assigning each pixel in a plurality of pixels on the sensor array to a corresponding group of an ordered set of groups on an illumination pixel array, wherein each group is defined by a set of p adjacent pixels on the illumination pixel array and wherein each group is defined by a group boundary by:
        (a) projecting and recording at least n images from a first set of n different binary patterns onto the surface, wherein a bright-to-dark or dark-to-bright transition between pixels in each of the n binary patterns occurs only at one or more of the group boundaries; and
        (b) projecting and recording at least m images from a second set of m different binary patterns onto the surface, wherein one or more bright-to-dark or dark-to-bright transitions between pixels in each of the m binary patterns are offset from one or more of the group boundaries;
    projecting and recording at least p different multiline images onto the surface, wherein each multiline image projects a line within each group;
    correlating lines in the recorded multiline images with lines in the projected multiline images according to the group map; and
    using the recorded at least p multiline images to form a surface contour image of the surface, wherein n and m are integers greater than or equal to 1 and p is an integer greater than or equal to 2.

2. The method of claim 1 further comprising storing the correlation in a computer-accessible memory, and generating surface contour data according to the stored correlation.

3. The method of claim 1 wherein the ratio of longest to shortest run lengths for the first set of n binary patterns is less than $2^{n-4}$.

4. The method of claim 1 wherein the first set of n binary patterns is projected so that each successive pattern changes by only one bit from the previous pattern.

5. The method of claim 1 wherein the ratio of longest to shortest run lengths for the first set of n binary patterns is less than $2^{n-4}$ and wherein the first set of n binary patterns is projected so that each successive pattern changes by only one bit from the previous pattern.

6. The method of claim 1 wherein the illumination pixel array is a liquid crystal device or a digital micromirror array device.

7. The method of claim 1, where patterns of the first set of different binary patterns, patterns of the second set of different binary patterns, and patterns of the at least p different multiline images are each different from each other.

8. The method of claim 1 wherein forming the group map further comprises obtaining and recording at least one dark field image and at least one flat field image.

9. The method of claim 2 further comprising displaying the surface according to the surface contour data.

10. A method for mapping a line of pixels in a sensor pixel array to a line of pixels in an illumination pixel array according to a surface, comprising:
    defining an ordered sequence of groups, wherein each group is defined by a set of p pixels that are adjacent along the line on the illumination pixel array, wherein p is an integer greater than or equal to 2;

assigning pixels along the line of pixels in the sensor pixel array to the defined groups of p adjacent pixels along the line on the illumination pixel array by:
  projecting and recording a first set of a plurality of different binary patterns including transitions indicative of boundaries between said groups of p adjacent pixels,
  projecting and recording a second set of one or more different binary patterns wherein one or more transitions in the second set are offset from the group boundaries, and
  projecting and recording at least one dark field image and at least one flat field image;
recording a third set of at least p multiline images projected onto the surface, wherein each of the projected different multiline images projects a single line of light at a time for each defined group of p adjacent pixels;
correlating lines in the recorded multiline images with lines in the projected multiline images according to the group assignment and the at least one dark and flat field images; and
storing the correlation as a mapping in a computer-accessible memory.

11. The method of claim 10 wherein the surface is a tooth.

12. The method of claim 10 wherein the first set of n binary patterns is projected so that each successive pattern changes by only one bit from the previous pattern.

13. The method of claim 10 wherein the ratio of longest to shortest run lengths for the first set of n binary patterns is less than $2^{n-4}$ and wherein the first set of n binary patterns is projected so that each successive pattern changes by only one bit from the previous pattern.

14. The method of claim 10 wherein the illumination pixel array is a liquid crystal device or a digital micromirror array device.

15. The method of claim 10, where patterns of the first set of different binary patterns, patterns of the second set of different binary patterns, and patterns of the at least p different multiline images are each different from each other.

16. The method of claim 10 further comprising displaying the surface according to the stored mapping.

17. A method for forming a surface contour image, comprising:
  forming a group map by assigning each pixel in a plurality of pixels on the sensor array to a corresponding group of an ordered set of groups on an illumination pixel array, wherein each group is defined by a set of p adjacent pixels in a row on the illumination pixel array, and wherein two adjacent groups share a group boundary; by:
    (a) projecting and recording at least n images from a first set of n binary patterns onto the surface, wherein a bright-to-dark or dark-to-bright transition between pixels in each of the n binary patterns occurs only at the group boundary; and
    (b) projecting and recording at least m images from a second set of m binary patterns onto the surface, wherein one or more bright-to-dark or dark-to-bright transitions between pixels in each of the m binary patterns are offset from the group boundary;
  projecting and recording a third set of at least p multiline images onto the surface, wherein each multiline image has, within each group of pixels in the ordered set of groups within the row on the illumination pixel array, a single bright pixel;
  correlating lines in the recorded multiline images with lines in the projected multiline images according to the group map, wherein n and m are integers greater than or equal to 1 and p is an integer greater than or equal to 2;
  storing the correlation in a computer-accessible memory;
  using the at least p multiline images to form a surface contour image; and
  displaying the surface contour image formed according to the stored correlation.

18. The method of claim 17 wherein the first set of n binary patterns is projected so that each successive pattern changes by only one bit from the previous pattern.

19. The method of claim 17 wherein forming the group map further comprises obtaining and recording at least one dark field image and at least one flat field image.

* * * * *